(12) United States Patent
Burke et al.

(10) Patent No.: US 9,339,030 B2
(45) Date of Patent: May 17, 2016

(54) FOAMABLE PESTICIDE COMPOSITIONS AND METHODS OF APPLICATION

(75) Inventors: Terrence R. Burke, St. Louis, MO (US); Henry Wayne Moran, St. Louis, MO (US); Jonathan D. Berger, St. Louis, MO (US); James H. Cink, St. Louis, MO (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 13/259,879

(22) PCT Filed: Aug. 24, 2010

(86) PCT No.: PCT/US2010/046515
§ 371 (c)(1),
(2), (4) Date: Dec. 7, 2011

(87) PCT Pub. No.: WO2011/025789
PCT Pub. Date: Mar. 3, 2011

(65) Prior Publication Data
US 2012/0149570 A1 Jun. 14, 2012

Related U.S. Application Data

(60) Provisional application No. 61/237,977, filed on Aug. 28, 2009.

(51) Int. Cl.
| | |
|---|---|
| A01N 25/04 | (2006.01) |
| A01N 25/06 | (2006.01) |
| A01N 25/16 | (2006.01) |
| A01N 25/30 | (2006.01) |
| A01N 47/02 | (2006.01) |

(52) U.S. Cl.
CPC ............... *A01N 25/16* (2013.01); *A01N 25/04* (2013.01); *A01N 25/06* (2013.01); *A01N 25/30* (2013.01); *A01N 47/02* (2013.01)

(58) Field of Classification Search
CPC ....... A01N 25/04; A01N 25/06; A01N 25/16; A01N 25/30; A01N 47/02
See application file for complete search history.

(56) References Cited

U.S. PATENT DOCUMENTS

| | | | |
|---|---|---|---|
| 3,131,154 A * | 4/1964 | Klausner | 516/19 |
| 3,713,404 A | 1/1973 | Lavo et al. | |
| 4,665,061 A * | 5/1987 | Riebel et al. | 514/89 |
| 4,822,779 A | 4/1989 | Hwang et al. | |
| 4,889,710 A | 12/1989 | Hagarty | |
| 4,945,107 A | 7/1990 | Minetti | |
| 4,999,126 A | 3/1991 | Meade | |
| 5,017,620 A | 5/1991 | Grassman et al. | |
| 5,194,264 A * | 3/1993 | Van Tonder | 424/405 |
| 5,482,733 A | 1/1996 | Abe et al. | |
| 5,527,760 A | 6/1996 | Rensing et al. | |
| 5,620,678 A | 4/1997 | Burke | |
| 5,814,325 A | 9/1998 | Rod | |
| 6,117,854 A | 9/2000 | Silverman et al. | |
| 6,139,858 A | 10/2000 | Fujimoto | |
| 6,300,348 B1 | 10/2001 | Sirinyan et al. | |
| 6,415,956 B1 | 7/2002 | Havlovitz | |
| 6,416,752 B1 | 7/2002 | Richardson et al. | |
| 6,755,400 B2 * | 6/2004 | Howe | 261/121.1 |
| 6,814,956 B2 | 11/2004 | Besser et al. | |
| 6,840,461 B1 | 1/2005 | Burke et al. | |
| 7,628,979 B1 | 12/2009 | Morales-Ramos et al. | |
| 7,960,354 B2 | 6/2011 | Huang et al. | |
| 8,013,164 B2 | 9/2011 | Loso et al. | |
| 8,153,560 B2 | 4/2012 | Langewald et al. | |
| 8,193,364 B2 | 6/2012 | Loso et al. | |
| 8,269,016 B2 | 9/2012 | Loso et al. | |
| 8,288,422 B2 | 10/2012 | Loso et al. | |
| 8,349,815 B2 | 1/2013 | Huang et al. | |
| 8,598,214 B2 | 12/2013 | Loso et al. | |
| 2001/0036935 A1 | 11/2001 | Renello et al. | |
| 2003/0108585 A1 | 6/2003 | Roe et al. | |
| 2003/0152605 A1 | 8/2003 | Martin et al. | |
| 2003/0220296 A1 | 11/2003 | Besser et al. | |
| 2004/0057977 A1 | 3/2004 | Gardner et al. | |
| 2004/0253287 A1 | 12/2004 | Denton | |
| 2006/0057075 A1 | 3/2006 | Arkin et al. | |
| 2006/0073180 A1 | 4/2006 | Steward | |
| 2007/0020304 A1 | 1/2007 | Tamarkin et al. | |
| 2007/0049496 A1 | 3/2007 | Messerschmidt et al. | |
| 2008/0051312 A1 | 2/2008 | Lestage et al. | |
| 2008/0118585 A1 | 5/2008 | Nouvel | |
| 2008/0139437 A1 | 6/2008 | Power | |
| 2008/0312085 A1 * | 12/2008 | Kordes et al. | 504/247 |
| 2010/0140368 A1 * | 6/2010 | de Lame et al. | 239/1 |
| 2011/0160054 A1 | 6/2011 | Breuningger et al. | |
| 2011/0224075 A1 | 9/2011 | Kordes et al. | |

FOREIGN PATENT DOCUMENTS

| | | |
|---|---|---|
| CN | 101081024 A | 12/2007 |
| EP | 0400914 A1 | 5/1990 |
| EP | 0400914 A1 | 12/1990 |
| JP | 03063201 | 3/1991 |
| JP | 5238903 A | 9/1993 |
| JP | 07048204 | 2/1995 |
| JP | 2000095605 | 4/2000 |
| JP | 2003238302 | 8/2003 |
| JP | 2006131529 | 5/2006 |
| JP | 2008115155 | 5/2008 |

(Continued)

OTHER PUBLICATIONS

JP 05-238903, machine-generated translation.*

(Continued)

*Primary Examiner* — John Pak
*Assistant Examiner* — Nathan W Schlientz
(74) *Attorney, Agent, or Firm* — Armstrong Teasdale LLP (57) ABSTRACT

Ready-to-use foamable pesticide compositions that contain a pesticide dispersed in a composition containing water, a co-solvent, surfactant and propellant. Methods for treating pests such as arthropods by contacting pests with such compositions are also provided.

19 Claims, 2 Drawing Sheets

(56) References Cited

FOREIGN PATENT DOCUMENTS

| | | |
|---|---|---|
| TW | 201005079 | 2/2010 |
| WO | 9106214 | 5/1991 |
| WO | 02052940 A1 | 7/2002 |
| WO | 02089579 | 11/2002 |
| WO | 02090320 | 11/2002 |
| WO | 02090321 | 11/2002 |
| WO | 2004006677 | 1/2004 |
| WO | 2005063694 | 7/2005 |
| WO | 2005068423 | 7/2005 |
| WO | 2005068432 | 7/2005 |
| WO | 2005085216 | 9/2005 |
| WO | 2007026965 | 3/2007 |
| WO | 2007043677 | 4/2007 |
| WO | 2007060839 | 5/2007 |
| WO | 2007079162 | 7/2007 |
| WO | 2007101540 | 9/2007 |
| WO | 2007104720 | 9/2007 |
| WO | 2007104720 A1 | 9/2007 |
| WO | 2007115644 | 10/2007 |
| WO | 2008066153 | 6/2008 |
| WO | 2008072743 | 6/2008 |
| WO | 2008072783 | 6/2008 |
| WO | 2008108491 | 9/2008 |
| WO | 2009036797 A1 | 3/2009 |
| WO | 2009126668 | 10/2009 |

OTHER PUBLICATIONS

BASF, Termidor SC Terminticide/Insecticide, 2005, Label, 12 pages.
Bayer Environmental Science, Suspend SC, 205, Label, 9 pages.
CN Office Action from corresponding CN Application No. 201080028973.6, Jan. 23, 2013.
Co-owned U.S. Appl. No. 12/769,320, filed Apr. 28, 2010 entitled "Pesticide Compositions and Applicators".
Co-owned U.S. Appl. No. 12/769,403, filed Apr. 28, 2010 entitled "Foamable Pesticide Compositions".
Co-owned U.S. Appl. No. 12/769,414, filed Apr. 28, 2010 entitled "Methods for Controlling Pests".
Harcros Chemicals Inc. T-Mulz(R) MSDS.
International Search Report and Written Opinion for International Application No. PCT/US2010/032795 mailed Jul. 21, 2010, 18 pages.
International Search Report and Written Opinion for PCT/US2010/032789, dated Jul. 15, 2011; 18 pages.
Kobayashi N., et al., Foamable Aerosol Agent for Exterminating Harmful Insects Such as Ant, Cockroach, Wood Louse and Stink Bug, XP002590413, 2 pages.
Konk Insecticide Foam, retrieved from internet: www.pestsupplystore.com/Pesticides/Labels/Konk-Foam-Label.pdf.
Kwaambwa, "Stability and phase separation behaviour of systems of particles in a medium with added polymer", retrieved from internet: http://www.wrc.org.za.
Material Safety Data Sheet Alpine Ant and Termite Foam, Whitmire Micro-Gen Research Laboratories, Inc., Apr. 6, 2006, 2 pages.
Material Safety Data Sheet for Fastout CS Foam, Whitmire Micro-Gen Research Laboratories, Inc., Nov. 21, 2006, 2 pages.
Material Safety Data Sheet for Perma-Dust, Whitmire Micro-Gen Research Laboratories, Jun. 2, 2004, Inc., 2 pages.
Material Safety Data Sheet for Premise Foam, Bayer Environmental Science, Jun. 12, 2006, 7 pages.
Material Safety Data for Tri-Die, Whitmire Micro-Gen Research Laboratories, Inc., Jul. 28, 2006, 2 pages.
MSDS: Xanthan gum; Nov. 20, 2008.
Narahashi et al. Hum Exp Toxicol. 2007, 26 (4), 361-366.
Non-Final Office action issued Jul. 31, 2012 for co-owned U.S. Appl. No. 12/769,403.
Office Action for U.S. Appl. No. 13/607,249 dated Jan. 28, 2013; 25 pages.
Pesticide Residues in Food—1997, retrieved from internet: http://www.inchem.org/documents/jmpr/jmpmono/v097pr09.htm.
Product Label for Alpine Ant and Termite Foam, Whitmire Micro-Gen Research Laboratories, Inc., 2009, 2 pages.
Product Label for Label for Fastout CS Foam, Whitmire Micro-Gen Research Laboratories, Inc., 2007, 2 pages.
Product Label for Perma-Dust, Whitmire Micro-Gen Research Laboratories, Inc., 2004 2 pages.
Product Label for Premise Foam, Bayer Environmental Science, May 13, 2004, 4 pages.
Product Label for Tri-Die, Whitmire Micro-Gen Research Laboratories, Inc., 2005, 2 pages.
Profoam Platinum, Nothing Else Stacks Up, 2008, Label, 3 pages.
Tech Notes for Perma-Dust and Tri-Die, Whitmire Micro-Gen Research Laboratories, Inc., Mar. 2000, 2 pages.
Vanderbilt, Xanthan Gum, 2000, Label, 16 pages.
"Hydroxyethyl cellulose—Technical Datasheet", Aug. 1, 2005, pp. 1-28, XP55036141, Retrieved from the Internet: URL:http://www.dow.com/assets/attachments/industry/building_construction/Cellosize_brochure.pdf [retrieved on Aug. 23, 2012].
Michael Ash et al: "Part II: Chemical Component Cross-Reference: "Shellac gem—Siloxanes and silicones"" In: "Handbook of Fillers, Extender, and Diluents (2nd Edition)", Jan. 1, 2007, Synapse Information Resources, Inc., http://www.knovel.com/web/portal/browse/display?_EXT_KNOVEL_DISPLAY_bookid=2652&VerticalID=0, XP55036156, ISBN: 978-1-61-583087-9, pp. 672-678.
Michael Ash et al: "Part II: Chemical Component Cross-Reference: Silica, amorphous precipitated-Silicone" In: "Handbook of Rheology Modifiers", Jan. 1, 2006, Synapse Information Resources, Inc., XP55036160, ISBN: 978-1-61-583088-6, pp. 1673-1676.
J W Jordan: "Organophilic Clay-Base Thickeners", Clays and Clay Minerals, vol. 10, No. 1, Jan. 1, 1961, pp. 299-308, XP55036197.
European Office Action regarding Application No. 10 715 479.1 dated Jan. 24, 2013, 6 pages.
Final Office Action regarding U.S. Appl. No. 12/769,414 dated Feb. 15, 2013, 31 pages.
European Office Action regarding Application No. 10 715 479.1 dated Aug. 30, 2012; 9 pages.
Final Office Action, U.S. Appl. No. 12/769,406, Mailing date Mar. 25, 2013, pp. 11.
Notice of Allowance, U.S. Appl. No. 12/769,403, Mailing date Jun. 17, 2013, pp. 10.
Final Office Action for U.S. Appl. No. 12/769,320 dated Apr. 25, 2013; 20 pages.
EP Office Action for Application No. 10 715 479.1 dated May 27, 2013; 7 pages.
Final Office Action for U.S. Appl. No. 13/607,249 dated Jul. 3, 2013; 23 pages.
Sciarra, John J. et al., "Aerosols," Kirk-Othmer Encyclopedia of Chemical Technology, vol. 1, 2001, pp. 769-787.
Advisory Action for U.S. Appl. No. 13/607,249 dated Sep. 11, 2013; 3 pages.
Non Final Office Action for U.S. Appl. No. 12/769,320 dated Aug. 22, 2013; 18 pages.
Final Office Action for U.S. Appl. No. 12/769,414 dated Oct. 8, 2013; 28 pages.
Japanese Office Action for Application No. 2012-508-651 dated Mar. 7, 2014; 3 pages.
The Pharmaceutics and Compounding Laboratory, Formulating Stable Suspensions, UNC Eshelman School of Pharmacy, Date Unknown, pp. 1 (http://pharmlabs.unc.edu/labs/suspensions/stable.htm).
Dr. Kishor Wasan Laboratory, Preparation of a Suspension, University of British Columbia, Date Unknown, pp. 2 (http://www.wasanlab.com/pharm/prep.html).
Victoria Junction et al., WHO Training Workshop on Pharmaceutical Development with Focus on Pediatric Formulations Apr. 16-20, 2007, pp. 36.
Kim et al., "Aerobic Soil Metabolism of Flupyrazofos", Pestic. Sci., 1998, pp. 237-243, vol. 54.
What is the difference between emulsifier and surfactant?, retrieved from Internet: http://wiki.answers.com/Q/What_is_the_difference_between_emulsifier_and_surfactant. Retrieved on Mar. 6, 2014.

(56) References Cited

OTHER PUBLICATIONS

Advisory Action for U.S. Appl. No. 12/769,414 dated Mar. 14, 2014; 3 pages.
Final Office Action for U.S. Appl. No. 12/769,320 dated Feb. 27, 2014; 17 pages.
Non-Final Office Action for U.S. Appl. No. 13/607,249 dayed Jun. 23, 2014; 16 pages.
Final Office Action for U.S. Appl. No. 12/769,320 dated Jun. 5, 2014; 18 pages.
Cellulose gum: retrieved from internet: http://www.ewg.org/skindeep/ingredient/701190/CELLULOSE_GUM. retrieved on Jun. 6, 2014.
Final Office Action for U.S. Appl. No. 13/607,249 dated Sep. 23, 2014; 11 pages.
Non-Final Office Action for U.S. Appl. No. 12/769,320 dated Oct. 9, 2014; 18 pages.
Final Office Action for U.S. Appl. No. 12/769,320 dated Feb. 26, 2015; 24 pages.

* cited by examiner

FOAMABLE PESTICIDE COMPOSITIONS AND METHODS OF APPLICATION

BACKGROUND

The field of the disclosure relates generally to pesticide compositions and, more particularly, to ready-to-use foamable compositions. The filed of the disclosure also relates to applicators and methods for applying the compositions that allow for tracking where the composition has been applied during use. The compositions of some embodiments of the present disclosure are well-suited for general pesticide applications and are particularly well-suited for treating and controlling arthropods including insects and, particularly, for treating termites, ants, cockroaches and beetles.

Insects and other arthropod pests can have negative effects on the quality of human life. For instance, when found in the home, insects and other arthropods can be a source of annoyance due purely to their presence. They may also spread disease and allergens. Additionally, when found on plants and crops, insects and other arthropods can destroy foliage and fruit, and may adversely affect plant and crop growth, quality, and yield.

Among insects which are particularly undesirable are termites, ants, cockroaches and beetles. Termites, for example, are well known for their destructive effects on residences, businesses and various other structures. The damage from termite infestations can result in large economic losses, structural safety concerns, and destruction of architecturally valuable structures. Some species of ants are known to damage crops and others may bite humans or pets as an attack or defense mechanism. Cockroaches may carry a number of organisms that cause disease and beetles are known to damage food and residential and commercial structures.

It is domestically and commercially common and desirable to control termites, ants and other crawling arthropods, such as cockroaches, beetles, earwigs, silverfish, crickets, spiders, centipedes, millipedes, scorpions, pillbugs and sowbugs, as well as various flying insects including flies, mosquitoes, gnats, moths, wasps, hornets, bees and the like using a pesticide. A broad range of compounds have been found to be toxic to insects and other arthropods such that formulations containing the compounds may be used for their control. In many instances, proper treatment includes application of such compositions to the entire exterior perimeter of structures to act as a barrier for entry of pests or to ensure that pests entering and exiting the structure contact the pesticide.

In such exterior applications, a homeowner or pest control professional applies the composition to an exterior surface of the structure, such as near the base thereof, and/or on the ground surface near the structure and/or on other exterior surfaces such as landscape timber or open area ground surfaces. Compositions used for conventional exterior applications are typically applied in liquid form, which renders it difficult for the person applying the treatment to readily determine which areas have been treated and which have not. This can result in under- or over-application of the composition.

There is a need for compositions, application devices and associated application methods that enable toxic and/or repellant compounds to be applied over broad surfaces such around the exterior perimeter of a building structure, landscape materials, ground surfaces, and the like. There is also a need for such compositions, application devices and application methods that enable persons applying the compositions to track where the composition has been applied during a treatment process.

SUMMARY

In one aspect of the present disclosure, a ready-to-use foamable pesticide composition includes water, a co-solvent, a propellant, a surfactant and a pesticide. The co-solvent may be selected from the group consisting of acetone, isopropyl alcohol and mixtures thereof and the propellant may be selected from the group consisting of dimethyl ether, carbon dioxide and mixtures thereof.

Another aspect of the present disclosure is directed to a pesticide applicator for applying pesticide to a surface. The applicator includes a container and a pesticide composition within the container. The pesticide composition includes water, a co-solvent, propellant and a pesticide. The co-solvent may be selected from the group consisting of acetone, isopropyl alcohol and mixtures thereof. The propellant may be selected from the group consisting of dimethyl ether, carbon dioxide and mixtures thereof.

In a further aspect of the present disclosure, a method for controlling pests includes contacting a surface with a pesticide composition. The composition includes water, a co-solvent, a propellant and a pesticide. The co-solvent may be selected from the group consisting of acetone, isopropyl alcohol and mixtures thereof. The propellant may be selected from the group consisting of dimethyl ether, carbon dioxide and mixtures thereof.

In yet another aspect of the present disclosure, a method for applying a pesticide to a target surface includes dispensing a pesticide composition onto a first area of the target surface. The pesticide composition includes a visual indicator to visually indicate where the pesticide composition has been applied after dispensing. Additional pesticide composition is dispensed onto a second area of the target surface at least in part different from the first area thereof based at least in part on the visual indicator present in the pesticide composition dispensed onto the first area of the target surface.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Among the provisions of the present disclosure are ready-to-use foamable compositions, applicators and methods for application and, in particular, application to control pests. It has been found that in embodiments of the present disclosure, a toxic chemical such as, for example, fipronil may generally be included in a composition that includes water, a co-solvent, a propellant and a surfactant. One particularly suitable composition includes water, acetone as a co-solvent and dimethyl ether and carbon dioxide as propellants.

It has been found that the foaming-action of the pesticide composition allows those applicating the composition to track where the pesticide composition has been applied which prevents over- and under-application of the composition. This is particularly beneficial when applying the composition in outdoor areas, such as about the perimeter of a building structure. The foaming composition, according to certain embodiments, is generally fast-breaking which allows the composition to visually disappear shortly after application such that it is unlikely that the formulation is visibly observed by persons other than the person applying the composition such as, for example, a homeowner.

Ready-To-Use Foamable Pesticide Compositions

In one embodiment of the present disclosure, a ready-to-use foamable pesticide composition is provided. For purposes of the present disclosure, "ready-to-use" refers to compositions that are not in a concentrate form but rather which may be applied without modification of the relative amounts of components within the product. In this regard, as used herein, the term "pesticide" refers to any substance or mixture for preventing, destroying, repelling, or mitigating any pest including insects, animals (e.g., mice, rats), plants (e.g., weeds), fungi, microorganisms (e.g., bacteria and viruses), pseudocoelomates (e.g., nematodes) and prions. The term "arthropodicide", which is a type of pesticide, is used herein to mean any substance or mixture for preventing, destroying, repelling, or mitigating arthropods. The term "insecticide", which is a type of pesticide, is used herein to mean any substance or mixture for preventing, destroying, repelling, or mitigating insects. The term "termiticide", which is a type of insecticide, is used herein to mean any substance or mixture for preventing, destroying, repelling, or mitigating termites.

Suitable pesticides which may be included in the compositions of the present disclosure (and particularly, suitable arthropodicides and/or insecticides) include the following list of compounds ("M compounds"):

(M1) Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

(M2) carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate;

(M3) pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;

(M4) juvenile hormone mimics: hydroprene, kinoprene, methoprene, fenoxycarb and pyriproxyfen;

(M5) nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022;

(M6) GABA gated chloride channel antagonist compounds: chlordane, endosulfan, gamma-HCH (lindane); ethiprole, fipronil, pyrafluprole and pyriprole (M7) chloride channel activators: abamectin, emamectin benzoate, milbemectin and lepimectin;

(M8) METI I compounds: fenazaquin, fenpyroximate, pyrimidifen, pyridaben, tebufenpyrad, tolfenpyrad, flufenerim, rotenone;

(M9) METI II and III compounds: acequinocyl, fluacyprim and hydramethylnon;

(M10) uncouplers of oxidative phosphorylation: chlorfenapyr and DNOC;

(M11) inhibitors of oxidative phosphorylation: azocyclotin, cyhexatin, diafenthiuron, fenbutatin oxide, propargite and tetradifon;

(M12) moulting disruptors: cyromazine, chromafenozide, halofenozide, methoxyfenozide and tebufenozide;

(M13) synergists: piperonyl butoxide and tribufos;

(M14) sodium channel blocker compounds: indoxacarb and metaflumizone;

(M15) selective feeding blockers: crylotie, pymetrozine and flonicamid;

(M16) mite growth inhibitors: clofentezine, hexythiazox and etoxazole;

(M17) chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron and triflumuron;

(M18) lipid biosynthesis inhibitors: spirodiclofen, spiromesifen and spirotetramat;

(M19) octapaminergic agonists: amitraz;

(M20) ryanodine receptor modulators: flubendiamide and the phtalamid compound (R)-, (S)-3-Chlor-N1-{2-methyl-4-[1,2,2,-tetrafluor-1-(trifluormethyl)ethyl]phenyl}-N2-(1-methyl-2-methylsulfonylethyl)phthalamide (M20.1);

(M21) isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M21.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M21.2), 4-[5-(3,5-Dichloro-phenyl)-5-trifluoromethyl-4,5-dihydro-isoxazol-3-yl]-2-methyl-N-[(2,2,2-trifluoro-ethyl-carbamoyl)-methyl]-benzamide (M21.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M21.4), 4-[5-(3,5-Dichlorophenyl)-5-trifluoromethyl-4,5-dihydro-isoxazol-3-yl]-N-[(methoxyimino)methyl]-2-methylbenzamide (M21.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M21.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M21.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M21.8);

(M22) anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M22.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M22.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M22.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M22.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M22.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M22.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M22.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M22.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M22.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M22.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M22.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M22.12);

(M23) malononitrile compounds: 2-(2,2,3,3,4,4,5,5-octafluoropentyl)-2-(3,3,3-trifluoro-propyl)malononitrile (CF2H—CF2-CF2-CF2-CH2-C(CN)2-CH2-CH2-CF3) (M23.1) and 2-(2,2,3,3,4,4,5,5-octafluoropentyl)-2-(3,3,4,4,4-pentafluorobutyl)-malonodinitrile (CF2H—CF2-CF2-CF2-CH2-C(CN)2-CH2-CH2-CF2-CF$_3$) (M23.2);

(M24) microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki* and *Bacillus thuringiensis* subsp. *Tenebrionis*;

(M25) aminofuranone compounds: 4-{[(6-Bromopyrid-3-yl)methyl](2-fluoroethyl)amino}furan-2(5H)-on (M25.1), 4-{[(6-Fluoropyrid-3-yl)methyl](2,2-difluoroethyl) amino}furan-2(5H)-on (M25.2), 4-{[(2-Chloro-1,3-thiazolo-5-yl)methyl](2-fluoroethyl)amino}furan-2(5H)-on (M25.3), 4-{[(6-Chloropyrid-3-yl)methyl](2-fluoroethyl) amino}furan-2(5H)-on (M25.4), 4-{[(6-Chloropyrid-3-yl) methyl](2,2-difluoroethyl)amino}furan-2(5H)-on (M25.5), 4-{[(6-Chloro-5-fluoropyrid-3-yl)methyl](methyl) amino}furan-2(5H)-on (M25.6), 4-{[(5,6-Dichloropyrid-3-yl)methyl](2-fluoroethyl)amino}furan-2(5H)-on (M25.7), 4-{[(6-Chloro-5-fluoropyrid-3-yl)methyl](cyclopropyl) amino}furan-2(5H)-on (M25.8), 4-{[(6-Chloropyrid-3-yl) methyl](cyclopropyl)amino}furan-2(5H)-on (M25.9) and 4-{[(6-Chloropyrid-3-yl)methyl](methyl)amino}furan-2 (5H)-on (M25.10);

(M26) botanically-derived oils and compounds: cinnamon oil, dill oil, mint oil, thyme oil, anabasine, azadirachtin, d-limonene, cinerin-I, cinerin-II, jasmolin-I, jasmolin-II, pyrethrin-I and pyrethrin-II;

(M27) various compounds: amidoflumet, benclothiaz, benzoximate, bifenazate, borax, bromopropylate, cyenopyrafen, cyflumetofen, chinomethionate, dicofol, fluoroacetate, pyridalyl, pyrifluquinazon, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy] methyl]-1,3,4,4a,5,6,6a,12,12a,12b-decahydro-12-hydroxy-4,6a,12b-trimethyl-11-oxo-9-(3-pyridinyl)-2H,11H-naphtho [2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds described above may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M22.1 to M22.6 have been described in WO 2008/72743 and WO 200872783 and M22.7 to M22.12 have been described in WO 2007/043677. The phthalamide M20.1 is known from WO 2007/101540. The alkynylether compound M27.1 is described in, for example, JP 2006131529. Organic sulfur compounds have been described in WO 2007/060839. The isoxazoline compounds M 21.1 to M 21.8 have been described in, for example, WO 2005/085216, WO 2007/079162, WO 2007/026965, WO 2009/126668 and WO 2009/051956. The aminofuranone compounds M25.1 to M25.10 have been described in, for example, WO 2007/115644. The pyripyropene derivative M 27.2 has been described in WO 2008/66153 and WO 2008/108491. The pyridazin compound M27.3 has been described in JP 2008/115155. Malononitrile compounds as M23.1 and M23.2 have been described in WO 02/089579, WO 02/090320, WO 02/090321, WO 04/006677, WO 05/068423, WO 05/068432 and WO 05/063694.

Suitable fungicides which may be included in the compositions of the present include the following list of compounds ("N compounds"):

(N1) respiration Inhibitors:

(N1a) inhibitors of complex III at Qo site (e.g. strobilurins):

strobilurins: azoxystrobin, dimoxystrobin, enestroburin, fluoxastro-bin, kresoxim-methyl, meto-minostrobin, orysastrobin, picoxy-strobin, pyraclostrobin, pyrametostrobin, pyraoxystrobin, pyribencarb, trifloxystrobin, methyl(2-chloro-5 [1-(3-methylbenzyl-oxy-imino)-ethyl]benzyl)-carba-mate and 2 (2-(3-(2,6-di-chlorophenyl)-1-methyl-allylidene-aminooxy-methyl)-phenyl)-2-methoxyimino-N methyl-acetamide;

oxazolidinediones and imidazolinones: famoxadone, fenamidone;

(N1b) inhibitors of complex II (e.g. carboxamides)

carboxanilides: benodanil, bixafen, boscalid, carboxin, fen-furam, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' tri-fluoro-bi-phenyl-2 yl)-3-difluoromethyl-1-methyl-1H-pyrazole-4 carboxamide, N-(4'-tri-fluoro-methyl-thiobi-phenyl-2-yl)-3 difluoromethyl-1-methyl-1H-pyrazole-4-carbox-amide and N-(2-(1,3,3-trimethyl-butyl)-phenyl)-1,3-dimethyl-5 fluoro-1H-pyrazole-4 carbox-amide;

(N1c) inhibitors of complex III at Qi site:
cyazofamid, amisulbrom;

(N1d) other respiration inhibitors (complex I, uncouplers)
diflumetorim;
nitrophenyl derivates: binapacryl, dinobuton, dinocap, fluazinam, nitrthal-isopropyl, tecnazen;
ferimzone;
organometal compounds: fentin salts, such as fentin-acetate, fentin chloride or fentin hydroxide;
ametoctradin;
silthiofam;

(N2) sterol biosynthesis inhibitors (SBI fungicides)

(N2a) C14 demethylase inhibitors (DMI fungicides, e.g. triazoles, imidazoles):
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothio-conazole, simeconazole, tebuconazole, tetraconazole, triadimefon, triadimenol, triticonazole, uniconazole;
imidazoles: imazalil, pefurazoate, oxpoconazole, prochloraz, triflumizole;
pyrimidines, pyridines and piperazines: fenarimol, nuarimol, pyrifenox, triforine;

(N2b) Delta 14-reductase inhitors (Amines, e.g. morpholines, piperidines
morpholines: aldimorph, dodemorph, dodemorph-acetate, fenpropimorph, tridemorph;
piperidines: fenpropidin, piperalin;
spiroketalamines: spiroxamine;

(N2c) inhibitors of 3-keto reductase
hydroxyanilides: fenhexamid;

(N3) nucleic acid synthesis inhibitors (N3a) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;

(N3b) DNA topisomerase inhibitors
oxolinic acid;

(N3c) nucleotide metabolism (e.g. adenosin-deaminase)
hydroxy (2-amino)-pyrimidines: bupirimate;

(N4) inhibitors of cell division and or cytoskeleton (N4a) tubulin inhibitors
benzimidazoles and thiophanates: benomyl, carbendazim, fuberidazole, thiabendazole, thiophanate-methyl;
triazolopyrimidines: 5-chloro-7 (4-methyl-piperidin-1-yl)-6-(2,4,6-trifluorophenyl)-[1,2,4]tri-azolo-[1,5a]pyrimidine (N4b) other cell division inhibitors
benzamides and phenyl acetamides: diethofencarb, ethaboxam, pencycuron, fluopicolide, zoxamide;

(N4C) actin inhibitors
benzophenones: metrafenone;

(N5) inhibitors of amino acid and protein synthesis (N5a) methionine synthesis inhibitors (aniline pyrimidines)
anilino-pyrimidines: cyprodinil, mepanipyrim, nitrapyrin, pyrimethanil;

(N5b) protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;

(N6) signal transduction inhibitors (N6a) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;

(N6b) G protein inhibitors (quinolines)
quinolines: quinoxyfen;

(N7) lipid and membrane synthesis inhibitors (N7a) phospholipid biosynthesis inhibitors (e.g.)
organophosphorus compounds: edifenphos, iprobenfos, pyrazophos;
dithiolanes: isoprothiolane;

(N7b) lipid peroxidation
aromatic hydrocarbons: dicloran, quintozene, tecnazene, tolclofos-methyl, biphenyl, chloroneb, etridiazole;

(N7c) carboxyl acid amides (CAA fungicides)
cinnamic or mandelic acid amides: dimethomorph, flumorph, mandiproamid, pyrimorph;
valinamide carbamates: benthiavalicarb, iprovalicarb, pyribencarb, valifenalate and N-(1-(1-(4-cyano-phenyl)-ethanesulfonyl)-but-2-yl)carbamic acid-(4-fluorophenyl)ester;

(N7d) Compounds affecting cell membrane permeability and fatty acids
carbamates: propamocarb, propamo-carb-hydrochlorid (N8) inhibitors with Multi Site Action (N8a) inorganic active substances
Bordeaux mixture, copper acetate, copper hydroxide, copper oxychloride, basic copper sulfate, sulfur;

(N8b) thio- and dithiocarbamates
ferbam, mancozeb, maneb, metam, methasulphocarb, metiram, propineb, thiram, zineb, ziram;

(N8c) organochlorine compounds (e.g. phthalimides, sulfamides, chloronitriles)
anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

(N8d) guanidines
guanidine, dodine, dodine free base, guazatine, guazatine-acetate, iminoctadine, iminoctadine-triacetate, iminoctadine-tris(albesilate);

(N8e) ahtraquinones
dithianon;

(N9) Cell wall synthesis inhibitors (N9a) Inhibitors of glucan synthesis
validamycin, polyoxin B;

(N9b) Melanin synthesis inhibitors
pyroquilon, tricyclazole, carpropamide, dicyclomet, fenoxanil;

(N10) Plant defense inducers (N10a) salicylic acid pathway
acibenzolar-S-methyl;

(N10b) others
probenazole, isotianil, tiadinil, prohexadione-calcium;
phosphonates: fosetyl, fosetyl-aluminum, phosphorous acid and its salts;

(N11) Unknown mode of action
bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3- difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-prop-oxy)-phenyl)-N-ethyl-N-methyl formamidine, N'-(5-difluoromethyl-2 methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-meth-yl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dim-ethyl-quinolin-4-yl ester and N-Methyl-2-{1-[(5-me-thyl-3-trifluoro-methyl-1H-pyr-azol-1-yl)-acetyl]-pip-eri-din-4-yl}-N-[(1R)-1,2,3,4-tetrahydro-naphthalen-1-yl]-4-thi-azolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-iso-propyl-3-oxo-4-ortho-tolyl-2,3-dihydro-pyrazole-1 carbo-thioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimeth-oxy-phenyl)-isoxazol-5-yl]-2-prop-2-ynyloxy-acetamide;

(N12) growth regulators abscisic acid, amidochlor, ancymidol, 6-benzylaminopurine, brassinolide, butralin, chlormequat (chlormequat chloride), choline chloride, cyclanilide, daminozide, dike-gulac, dimethipin, 2,6-dimethylpuridine, ethephon, flumetralin, flurprimidol, fluthi-acet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

(N13) biological control agents antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), Ulocladium oudemansii (e.g. the product BOTRY-ZEN from BotriZen Ltd., New Zealand), Chitosan (e.g. ARMOUR-ZEN from BotriZen Ltd., New Zealand).

Suitable herbicides that may be incorporated into the pesticide compositions of the present disclosure include the compounds listed below ("P Compounds")

(P1) acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

(P2) amino acid derivatives: bilanafos, glyphosate, glufosinate, sulfosate;

(P3) aryloxyphenoxypropionates: clodinafop, cyhalofop-butyl, fenoxaprop, fluazifop, haloxyfop, metamifop, propaquizafop, quizalofop, quizalofop-P-tefuryl;

(P4) Bipyridyls: diquat, paraquat;

(P5) (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

(P6) cyclohexanediones: butroxydim, clethodim, cycloxydim, profoxydim, sethoxydim, tepraloxydim, tralkoxydim;

(P7) dinitroanilines: benfluralin, ethalfluralin, oryzalin, pendimethalin, prodiamine, trifluralin;

(P8) diphenyl ethers: acifluorfen, aclonifen, bifenox, diclofop, ethoxyfen, fomesafen, lactofen, oxyfluorfen;

(P9) hydroxybenzonitriles: bomoxynil, dichlobenil, ioxynil;

(P10) imidazolinones: imazamethabenz, imazamox, imazapic, imazapyr, imazaquin, imazethapyr;

(P11) phenoxy acetic acids: clomeprop, 2,4-dichlorophenoxyacetic acid (2,4-D), 2,4-DB, dichlorprop, MCPA, MCPA-thioethyl, MCPB, Mecoprop;

(P12) pyrazines: chloridazon, flufenpyr-ethyl, fluthiacet, norflurazon, pyridate;

(P13) pyridines: aminopyralid, clopyralid, diflufenican, dithiopyr, fluridone, fluoroxypyr, picloram, picolinafen, thiazopyr;

(P14) sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1 ((2-chloro-6-propyl-imidazo[1,2-b]pyridazin-3-yl)sulfonyl)-3-(4,6-dimethoxy-pyrimidin-2-yl)urea;

(P15) triazines: ametryn, atrazine, cyanazine, dimethametryn, ethiozin, hexazinone, metamitron, metribuzin, prometryn, simazine, terbuthylazine, terbutryn, triaziflam;

(P16) ureas: chlorotoluron, daimuron, diuron, fluometuron, isoproturon, linuron, metha-benzthiazuron, tebuthiuron;

(P17) other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

(P18) others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)- pyridine-2-carboxylic acid methyl ester, and 4-amino-3-chloro-6-(4-chloro-3-dimethylamino-2-fluoro-phenyl)-pyridine-2-carboxylic acid methyl ester.

The composition may include one or more of the above-listed pesticides in any combination without limitation.

In one embodiment, the pesticide is fipronil. Fipronil is known chemically as (±)-5-amino-1-(2,6-dichloro-α,α,α-trifluoro-p-tolyl)-4-trifluoromethylsulfinylpyrazole-3-carbonitrile. The structure of fipronil is illustrated in Formula (I) below, Fipronil has been found effective in treatment of many pests including, for example, termites, ants, beetles, cockroaches, fleas, ticks, mole crickets, thrips, rootworms and weevils. Generally, fipronil may be toxic to termites at a dose of 2 nanograms per termite and may be toxic to ants at a dose of about 1 nanogram per ant. Suitable commercially available sources of fipronil include, for example, technical grade fipronil and TERMIDOR® SC.

Many pesticide actives such as fipronil are substantially non-soluble in many solvents including water-based solvents. Generally, surfactants of the present disclosure act to disperse the pesticide in the continuous phase of the composition. In certain embodiments, the pesticide composition of embodiments of the present disclosure is substantially clear and the pesticide is not visually observed. Without being bound to any particular theory, it is believed that the composition forms a microemulsion. In certain embodiments, the composition produces a uniform foam upon application without the pesticide being visible (i.e., an infused foam is produced).

The amount of pesticide utilized in the pesticide composition may vary depending on the intended use of the composition including, for example, the pests intended for control. In some embodiments, a pest is contacted with the pesticide composition in a pesticidally effective amount. For purposes of the present disclosure, a "pesticidally effective amount" of the composition includes amounts that repel the pest and may include, in other embodiments, amounts of the composition that kill the pest. In certain embodiments, the composition comprises at least about 0.005% by weight pesticide and, in other embodiments, at least about 0.01%, at least about 0.1%, at least about 0.5% or at least about 1% by weight pesticide. In some embodiments, the composition includes from about 0.05% to about 5% by weight pesticide or from about 0.05% to about 1% by weight pesticide.

When fipronil is used as the pesticide, the composition may include at least about 0.01% by weight fipronil and, in other embodiments, at least about 0.1% by weight fipronil, at least about 0.3% or even at least about 0.5% by weight fipronil. In various other embodiments, the composition includes from about 0.01% to about 1.5% by weight fipronil, from about 0.1% to about 1% by weight fipronil or from about 0.3% to about 1% by weight fipronil.

As described above, the pesticide may be dispersed throughout the continuous phase of the composition. In some embodiments, the composition includes water and a co-solvent selected from acetone and isopropyl alcohol or a mixture thereof. As it is desirable to limit the amount of volatile organic compounds in the composition, in some embodiments the composition does not include isopropyl alcohol but rather includes acetone as a co-solvent. The composition may include at least about 30% by weight water and, in other embodiments, at least about 50%, from about 30% to about 90%, from about 40% to about 80% or from about 50% to about 70% by weight water. In combination with water or as the only component of the continuous phase, the composition may include at least about 5% by weight acetone and, in other embodiments, at least about 15%, at least about 20%, from about 5% to about 50%, from about 10% to about 40% or from about 20% to about 30% by weight acetone. If isopropyl alcohol is used in the composition, it may be used in about the same amounts as described for acetone.

As packaged, the composition may also include propellants which pressurize the storage container and which help create foaming action upon application of the composition. The total amount of propellants in the pesticide composition may be at least about 1% by weight of the composition. Suitable propellants include, for example, propane, isobutane, dimethyl ether, difluoroethane, tetrafluoroethane, carbon dioxide and mixtures thereof. In certain embodiments, dimethyl ether and carbon dioxide are used as propellants. Dimethyl ether and carbon dioxide are generally soluble in water/acetone mixtures. This solubility allows the composition to be applied without shaking the container in which it is stored. In compositions that include water, acetone as a co-solvent and dimethyl ether and carbon dioxide as propellants, the composition may be applied as a fast-breaking foam. Such fast-breaking compositions allow those applying the composition to track where the composition has been applied but allows the composition to dissipate prior to public viewing.

In other embodiments, it is desirable for the pesticide composition to be capable of being in a foam phase after application and to remain in the foam phase for less than about 10 minutes after application. Such compositions are generally referred to herein as being "fast-breaking." The composition is generally in the "foam phase" when at least above 5% by volume of the initial volume of the applied composition may be characterized by a "froth" or "foam" consistency. Generally, this is desirable when the pesticide composition is to be applied outdoors such as, for example, application to exterior surfaces exposed to typical weather conditions.

In some embodiments, the pesticide composition is capable of remaining in the foam phase for less than about 10 minutes after application and, in other embodiments, remaining in the foam phase for less than about 5 minutes, for less than about 2 minutes, for less than about 1 minute, for less than about 30 seconds and even less than about 15 seconds after application. In some embodiments, the pesticide composition foams from the time of application to from about 1 second to about 5 minutes, from about 1 second to about 1 minute, from about 5 seconds to about 1 minute or from about 5 seconds to about 30 seconds. The rate at which the foam breaks may generally be controlled by selecting the amount of surfactant included in the composition with higher amounts of surfactant corresponding to lower foam breaking rates. The length of time the composition foams may also be increased by using hydrocarbon propellants or by using thickening agents such as, for example, xantham gum.

In this regard, the amount of time the pesticide composition remains in a foam phase may vary somewhat according to the surface to which it is applied, the distance from the surface during application, the rate at which the application was applied (e.g., grams per linear foot) and the apparatus used to apply the composition (e.g., the actuator used to apply the composition). The breaking times recited herein refer to the time the composition remains in the foam phase when applied to a concrete surface at a rate of from about 0.3 to about 0.7 g/foot (about 1.0 to about 2.3 g/meter) at a distance from the surface ranging from about 2 inches to about 4 inches (about 5 to about 10 cm). The actuator used during testing may be a fan spray actuator (e.g., Summit Fan Spray 77820 actuator (Summit Europe CV; Almere-Buiten, Netherlands)). It should be understood that other surfaces, distances and rates may provide equivalent break times without limitation.

In some embodiments, the pesticide composition is capable of remaining in the foam phase for less than about 10 minutes or even less than 5 minutes or less than one minute after application regardless of the surface to which it is applied, the rate at which it is applied, the distance from the surface during application and/or the actuator used during application.

The fast-breaking foam broadly acts as a visual indicator (e.g., as opposed to conventional compositions that are applied as a liquid which is difficult to see once applied, particularly to a ground surface) to allow the individual applying the composition to readily see areas that have been treated, thus reducing the risk of over application or possible treatment of unintended areas. The foam breaks down or disintegrates relatively quickly to promote the drying of the treatment area, thus reducing the potential for unintended dislodging or transfer of the wet material by humans, animal traffic and/or wind following application. There is also no undesired or unsightly visual indicator remaining once the treatment is completed.

While in some embodiments of the present disclosure the composition is configured to deliver a visual indicator in the form of a foam, it should be understood that other visual indicators instead, or additionally, may be provided in the composition without departing from the scope of this disclosure. For example, in some embodiments the composition may be deliverable as either a liquid or a foam (or a powder) and may include a visual indicator in the form of a colorant to allow the person applying the treatment to track where applications have been made. In particular such embodiments the colorant may suitably fade or disappear shortly after application (e.g., within the same timing requirements as the fast-breaking foam discussed above).

Generally, the pesticide composition expands as it is applied and transitions to the foam phase. The foamable pesticide composition may be characterized by a foam expansion ratio of at least about 2:1. In other embodiments, the composition is characterized by a foam expansion ratio of at least about 10:1 or even at least about 25:1. In various other embodiments, the ready-to-use foamable pesticide composition is characterized by a foam expansion ratio of from about 2:1 to about 60:1 or from about 10:1 to about 40:1.

The composition may include one or more surfactants and, in some embodiments, a non-ionic surfactant. Suitable non-ionic surfactants include polyethoxylated castor oil and polysorbates. Suitable polysorbates include polyoxyethylene (20) sorbitan monooleate which is commercially known as Polysorbate 80 or Tween® 80. Polyethoxylated caster oils may be prepared by reacting castor oil with ethylene oxide. One suitable polyethoxylated castor oil is T-Det® C-40, commercially available from Harcros Chemicals Inc. (Kansas City, Kans.). Polyethoxylated caster oil may be used with one or more other surfactants without limitation or may be the only surfactant used in the composition.

The composition may include at least about 0.5% surfactants by weight of the composition and, in other embodiments, includes at least about 1%, at least about 3% or even at least about 5% surfactants by weight of the composition. In some embodiments, the composition includes from about 0.5% to about 15% surfactants by weight of the composition, from about 1% to about 10% or from about 4% to about 8% surfactants by weight of the composition.

The ready-to-use pesticide compositions of embodiments of the present disclosure may also include one or more preservative compounds. The preservative compounds act to prevent corrosion of the container which holds the pesticide composition. Suitable preservatives include sodium benzoate, benzoic acid and potassium bicarbonate. In some embodiments, the composition includes benzoic acid and potassium bicarbonate as preservatives.

The total amount of preservative compounds in the composition may be at least about 0.01% by weight of the composition and, in other embodiments, at least about 0.1% by weight of the composition or even at least about 0.15% by weight of the composition. In various other embodiments, the total amount of preservative compounds in the composition is from about 0.01% to about 0.4% by weight of the composition or from about 0.1% to about 0.4% by weight of the composition.

In certain embodiments of the present disclosure, the pesticide composition contains a pesticide stabilizer compound. Such compounds prevent or slow the rate at which the pesticide breaks down and loses its pesticidal effectiveness. Generally, in embodiments where fipronil is used as the pesticide, the stabilizer compound maintains a pH of the composition below 8, at which fipronil is more active. The pesticide stabilizer compound may be an organic acid. In some embodiments, the stabilizer compound is citric acid. The total amount of stabilizer compounds in the composition may be at least about 0.005% by weight of the composition. In various other embodiments, the total amount of pesticide stabilizer compounds in the composition is from about 0.005% to about 5% by weight of the composition, from about 0.005% to about 0.1% by weight of the composition or from about 0.005% to about 1% by weight of the composition.

In one or more embodiments, the composition is characterized by a pH of from about 6.5 to about 8 and, in other embodiments, by a pH of from about 7 to about 7.25. If the composition has a pH below about 6.5 to about 7, the container housing the composition may corrode with lower pH's corresponding to a higher rate of corrosion. Also, in embodiments where fipronil is used as the pesticide, fipronil tends to be more active at a pH below about 8. The composition may be characterized by a pH other than those listed without departing from the scope of the present disclosure.

Generally, the composition is prepared by mixing all ingredients other than propellants in their relative proportions. All mixing can be done at room temperature. Once mixed, the composition is added to a suitable container and one or more propellants may be added if desired.

Generally, the composition is applied to a surface such as the perimeter of a structure. Once applied, the composition may be in a foam phase. The foam composition may disintegrate into a liquid which dries to form dried particulate pesticide residue on the treated surface. The pesticide residue may act as a repellant to the target pests or may be toxic such that the pests are killed upon contact with the dried particulate pesticide.

Pesticide Applicator

Embodiments of the ready-to-use pesticide composition described above may be incorporated into a pesticide applicator utilized for applying a pesticide to pests. Generally, the applicator may include a container and a pesticide composition within the container. The pesticide composition may include water, a co-solvent (e.g., acetone and/or isopropyl alcohol), a propellant (e.g., dimethyl ether and/or carbon dioxide), a surfactant and a pesticide (e.g., fipronil). Other optional additives include preservatives and stabilizers as described above.

Suitable containers may be constructed of, for example, three-piece tinplate, aluminum and PET-lined steel containers. The pesticide composition may be pressurized within the container by addition of a propellant. The total amount of propellants in the pesticide composition may be at least about 1% by weight of the composition and, in another embodiment, is at least about 5% by weight of the composition. The total amount of propellants in the pesticide composition may be from about 1% to about 12% by weight or even about 3% to about 10% by weight. As stated above, suitable propellants include propane, isobutane, dimethyl ether, difluoroethane, tetrafluoroethane, carbon dioxide and mixtures thereof. In another embodiment, the composition includes dimethyl ether and carbon dioxide as propellants. The propellants may be compressed gases, soluble gases or liquified gases. In some embodiments, the propellant is a liquified hydrocarbon selected from the group consisting of propane, isobutane, dimethyl ether, difluoroethane and tetrafluoroethane. In certain embodiments, dimethyl ether is the only hydrocarbon propellant used in the composition.

Generally, if the propellants are soluble in the continuous phase (e.g., dimethyl ether in water) the composition does not need to be shook prior to use. Moreover, providing propellant as the means for delivering the composition from the container allows the composition to be applied while the container is inverted or at any other orientation (including upright) during application.

Figure 1:
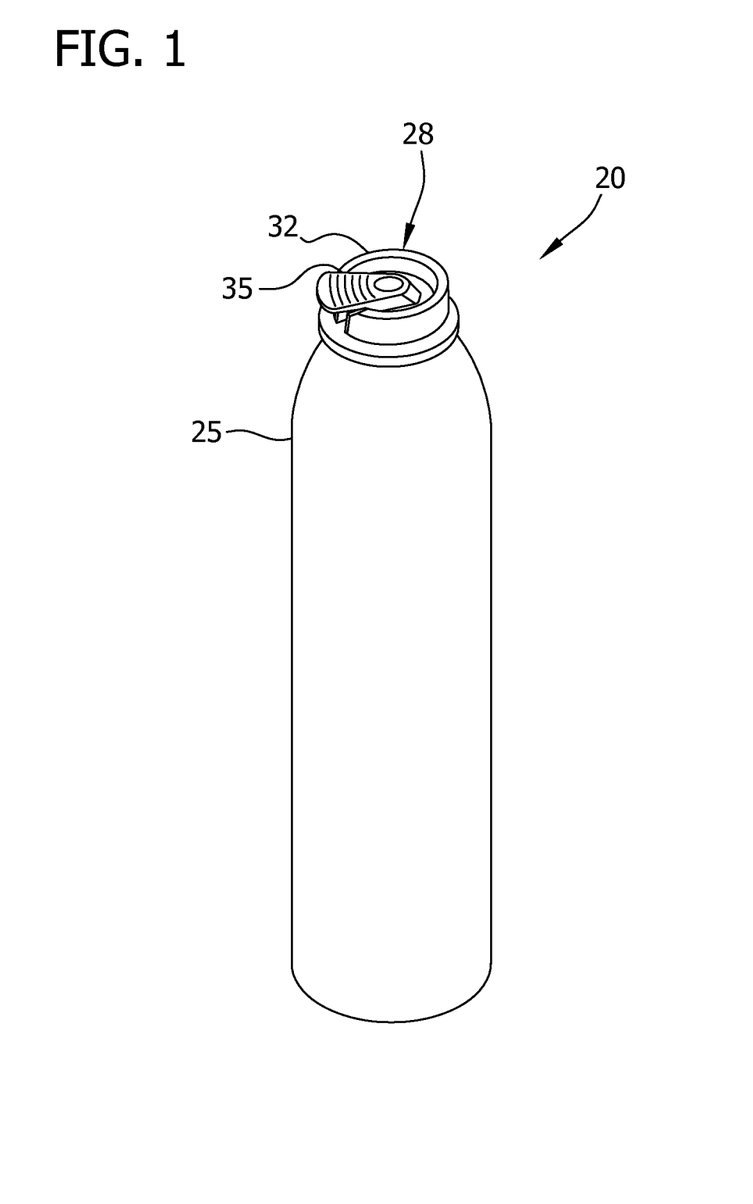
FIG. 1 is a front-side view of an applicator according to one embodiment of the present disclosure.

Referring now to FIG. 1, one embodiment of a suitable pesticide applicator for storage and application of pesticide compositions of embodiments of the present disclosure is generally referenced as numeral 20. The applicator 20 includes a container 25 containing a pesticide composition (not shown) as described above. In various embodiments, the pesticide composition includes water, a co-solvent, a propellant, a surfactant and a pesticide as described above under the section entitled "Ready-to-use Foamable Pesticide Compositions." Thus, no additional water or other solvent needs to be added to the composition shortly before or at the time of application.

The illustrated pesticide applicator 20 includes a cap 28 with an actuator 35 for regulating the flow of the pesticide composition from the container 25. The actuator 35 is sized and shaped for activation by a pressing force that may be provided by a human finger or suitable device. Suitable actuators include, for example, fan spray actuators (e.g., Summit Fan Spray 77820 actuator (Summit Europe CV; Almere-Buiten, Netherlands)). The applicator 20 includes one or more exhaust ports (not shown) configured for delivering the composition from the container in a desired treatment pattern. For example, in various suitable embodiments, the one or more exhaust ports are configured such that the composition is applied to the treatment surface in a relatively wide pattern as opposed to a narrow stream or random spray. It is understood, however, that the one or more exhaust ports may be configured to deliver the composition according to other patterns, or a random spray pattern, without departing from the scope of this disclosure.

Figure 2:
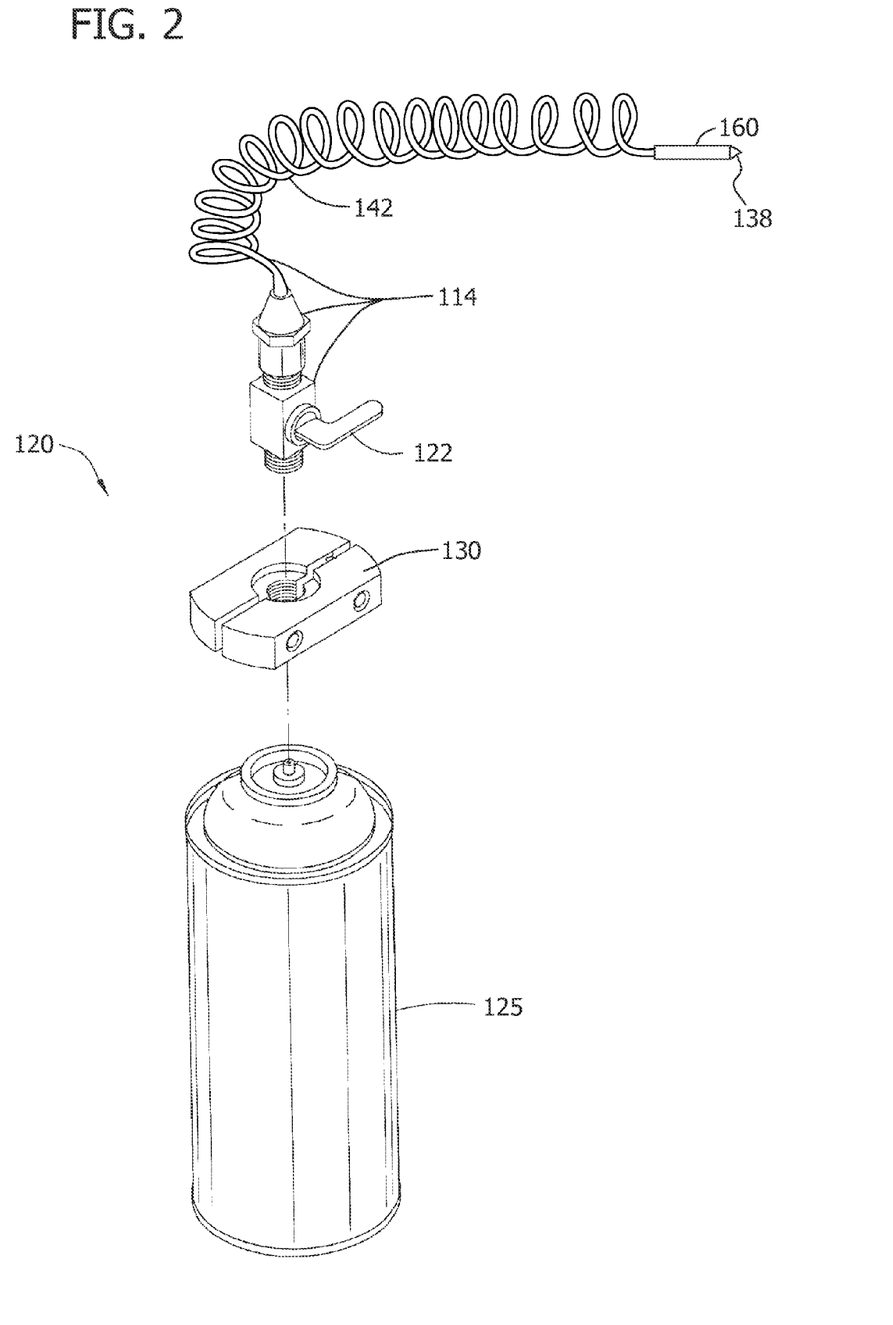
FIG. 2 is an exploded perspective view of a pesticide applicator according to a second embodiment of the present disclosure.

A second embodiment of an applicator of the present disclosure is illustrated in FIG. 2. The pesticide applicator 120 includes a container 125 (e.g., aerosol can) with an internal valve (not shown), an adaptor clamp 130 and a delivery system 114 as disclosed in U.S. Pat. No. 6,840,461 which is incorporated herein by reference for all relevant and consistent purposes. As shown, the delivery system 114 includes a coiled hose 142 (which optionally may or may not be extendible), wand 160 and exhaust port 138; however, it should be understood that other delivery systems may be used without departing from the scope of the present disclosure. The composition is dispensed upon activation of the actuator 122. Suitable wands (including wands used with other containers and applicators) may be a variety of lengths (e.g., about 10 inches to about 25 inches (about 25 cm to about 64 cm). The delivery system (e.g., assembly gun) may be obtained commercially from B&G Equipment Company (Jackson, Ga.) and the wand may be obtained from Spraying Systems Company (Wheaton, Ill.). A suitable nozzle for use in perimeter applications (i.e., fast-breaking foams) is a TJet 650033 nozzle. As appreciated by those of skill in the art, the nozzle may be selected to influence or control the amount of time the foam remains in the foam-phase. Containers other than aerosol cans as shown in FIG. 2 may be used without departing from the scope of the present disclosure.

In other embodiments, the applicator may include a hand-held container and spray pump that is actuated by hand. A suitable pump spraying apparatus is illustrated and described in U.S. Pat. No. 6,415,956 which is incorporated herein for all relevant and consistent purposes. In still other embodiments, the applicator may be any suitable spray-type applicator, whether pump operated, electrically operated, hydraulically operated or manually operated, and remain within the scope of this disclosure.

Application Methods

In various embodiments of a method for controlling pests, the pests are suitably contacted with a pesticidally effective amount of a composition comprising water, a co-solvent (e.g., acetone and/or isopropyl alcohol), a propellant (e.g., dimethyl ether and/or carbon dioxide), a surfactant and a pesticide (e.g., fipronil). Other optional additives include preservatives and stabilizers as described above.

The pesticide composition is well suited for application to the exterior of commercial or residential structures and in some embodiments for application to the interior of such structures as well. For example, in one embodiment of a method for controlling pests, a suitable applicator such as that described above and illustrated in FIG. 1 or in FIG. 2 is used to apply the composition to a target surface, such as the ground and/or exterior surface of a building structure, landscaping materials, and/or about any outdoor area (e.g., a garden area, a treed area, wooden fence posts, etc.). The composition is suitably applied in a predetermined pattern or at least an orderly or sequential pattern (e.g., along a circumferential path around a building structure) along a path of treatment. For example, the composition may be applied in sequential, side-by-side rows that are normal to or otherwise not parallel to the path of treatment. In other embodiments, the composition may be applied in a single continuous line along the path of treatment, or intermittent, generally end-facing-end lines along the path of treatment.

During application, the visual indicator provided by the fast-breaking foaming-action of the composition allows the individual applying the composition to readily and temporarily determine by visible inspection where the composition has been applied and where next to apply the composition to facilitate complete coverage of the target surface without over-application of the composition.

In suitable methods for using the pesticide composition, the composition may be dispensed onto a first area of a target surface so as to provide a visual indicator to visually indicate where the pesticide composition has been applied after dispensing. Additional pesticide composition may be dispensed onto a second area of the target surface which is at least in part different from the first area of the surface. The additional pesticide composition is dispensed based at least in part on the visual indicator present in the pesticide composition dispensed onto the first area of the target surface.

In embodiments wherein the pesticide is toxic to arthropods such as ants and termites, perimeter application ensures that pests which cross the pesticide barrier contact the pesticide and are deterred or killed before or upon entry into the structure. In embodiments wherein the pesticide is a repellant to arthropods, the barrier acts to keep pests from crossing the barrier and entering the structure. Suitable pesticides may be toxic and/or repellant. In some embodiments, the composition includes more than one pesticide compound and, optionally, one compound is that repellant and one compound that is toxic to arthropods.

Generally, in embodiments wherein the pesticide is toxic rather than repellant, the pest does not contact the pesticide composition upon application of the composition but rather after several hours or even days after application of the composition. For instance, the pest may contact the pesticide after about 1 minute after application, after about 5 minutes or even after about 30 minutes after application. Generally, the pesticide composition maintains its activity such that it is toxic to pests that contact the composition after about 1 hour after application, after about 12 hours after application, after about 1 day after application, after about 3 days after application, after about 7 days after application or even after about 30 days or more after application.

The formulation components may be adjusted (e.g., the amount of surfactant in the pesticide composition may be selected) to cause the composition to remain in the foam phase for a minimum target time or, as in another embodiment, a maximum target time. In certain embodiments where a maximum time the composition remains in the foam phase is desired, the composition may remain in a foam phase for less than about 10 minutes after application, for less than about 5 minutes, for less than about 2 minutes, for less than about 1 minute, for less than about 30 seconds or even less than about 15 seconds after application. In some embodiments, the pesticide composition remains in the foam phase for from about 1 second to about 5 minutes, for from about 1 second to about 1 minute, for from about 5 seconds to about 1 minute or from about 5 seconds to about 30 seconds after application.

In this manner, the foam remains visible for a sufficient time such that the person applying the composition may use the foam as a guide to determine which areas have been treated and which have not, but allows the foam to break in a sufficiently short time so that the foam does not remain publicly visible after the person applying the composition is finished with the application process or at least within a short period thereafter. Fast-breaking foams also reduce the likelihood of the foam blowing away in the wind and reduce the amount of foam that collects on the exhaust port of the dispensing device.

While compositions, applicators and methods of embodiments of the present disclosure are generally described as being a microemulsion with a continuous phase with the pesticide dispersed throughout the continuous phase, it should be understood that in certain embodiments of the present disclosure, the continuous phase acts as a solvent in which the pesticide is dissolved.

Generally, the ready-to-use pesticide compositions, pesticide applicators and methods for controlling pests of embodiments of the present disclosure are suitable for treatment and control of pest populations generally. In several embodiments the pest is an arthropod and, in another embodiment, is an insect. The target pest may be selected from the group consisting of termites, ants, cockroaches, beetles, earwigs, silverfish, crickets, spiders, centipedes, flies, mosquitoes, gnats, moths, wasps, hornets, bees, centipedes, millipedes, scorpions, pillbugs, sowbugs and the like. In one embodiment, the pest is a termite and, in another embodiment, the pest is an ant.

While compositions, applicators and methods of embodiments of the present disclosure are generally described with reference to the listed actives, it should be understood that, in other embodiments, other pesticides may be included in combination or in place of these compounds.

While compositions, applicators and methods of embodiments of the present disclosure are generally described with reference to perimeter application of the composition, it should be understood that the compositions may alternatively or in addition be applied to any exterior target surface such as landscaping materials, open ground space away from the structures, areas around fence posts or other wood structures, and the like. It is also understood that the composition may also be applied to the interior of building structures, including for example in void spaces, cracks, crevices, crawl spaces, hard-to-reach areas and the like.

EXAMPLES

Example 1

Preparation of a Foamable Pesticide Composition

Acetone (161.21 g; ExxonMobil Chemical (Houston, Tex.)) was weighed out in a mixing vessel and fipronil (4.82 g with about 88.75% active fipronil; BASF (Germany)) was mixed in until dissolved. Benzoic acid (0.99 g; EMD Chemicals (Gibbstown, N.J.)) was also added and dissolved. Polyethoxylated castor oil sold under the brand name T-DET® C-40 (36.82 g; Harcros Chemicals Inc. (Kansas City, Kans.)) was added and mixed until dispersed. In a separate mixing vessel deionized water (391.64 g) was weighed out and potassium bicarbonate (4.52 g; Armand Products Co. (Princeton, N.J.)) was mixed until dissolved. The water and bicarbonate mixture was added to the acetone mixture and mixed until the composition was uniform.

The mixture was added to a nickel tinplate DOT 2Q quality container (22 fl. oz. (651 ml)) lined with polyethylene terephthalate. Dimethyl ether propellant (38.6 g) and carbon dioxide (6.4 g) were added to the composition within the container. An actuator for dispensing the composition through an exhaust port was attached. The composition produced a consistent foam that dissipated within about 30 seconds. The composition was clear and uniform (i.e., particulate fipronil was not observed when the composition was evaluated in a glass aerosol). The relative proportions of all ingredients are shown in Table 1 below.

TABLE 1

Relative proportions of ingredients used to prepare
the pesticide composition of Example 1.

| Component | Inclusion (wt %) |
|---|---|
| Particulate Fipronil | 0.7324 (0.650 active) |
| Acetone | 24.5176 |
| Polyethoxylated Castor Oil | 5.6000 |
| Benzoic Acid | 0.1500 |
| Potassium Bicarbonate | 0.6875 |
| Water | 59.5625 |
| Dimethyl Ether | 7.5000 |
| Carbon Dioxide | 1.2500 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A ready-to-use foamable pesticide composition comprising:
   water;
   a co-solvent comprising acetone in an amount of from about 5% to about 50% by weight;
   a propellant selected from the group consisting of dimethyl ether, carbon dioxide and mixtures thereof;
   polyethoxylated castor oil in an amount of greater than 5% by weight; and
   a pesticide.

2. The ready-to-use foamable pesticide composition as set forth in claim 1 wherein acetone, dimethyl ether and carbon dioxide form a continuous phase and the pesticide is dispersed throughout the continuous phase.

3. The ready-to-use foamable pesticide composition as set forth in claim 1 wherein the composition is a microemulsion.

4. The ready-to-use foamable pesticide composition as set forth in claim 1 wherein the composition is capable of being in a foam phase after application and remaining in the foam phase for less than about 10 minutes after application.

5. The ready-to-use foamable pesticide composition as set forth in claim 1 wherein the pesticide is an arthropodicide selected from the group consisting of (M1) organo(thio)phosphate compounds selected from the group consisting of acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion; (M2) carbamate compounds selected from the group consisting of aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; (M3) pyrethroid compounds selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin; (M4) juvenile hormone mimics selected from the group consisting of hydroprene, kinoprene, methoprene, fenoxycarb and pyriproxyfen; (M5) nicotinic receptor agonists/antagonists compounds selected from the group consisting of acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022; (M6) GABA gated chloride channel antagonist compounds selected from the group consisting of chlordane, endosulfan, gamma-HCH (lindane), ethiprole, fipronil, pyrafluprole and pyriprole; (M7) chloride channel activators selected from the group consisting of abamectin, emamectin benzoate, milbemectin and lepimectin; (M8) METI I compounds selected from the group consisting of fenazaquin, fenpyroximate, pyrimidifen, pyridaben, tebufenpyrad, tolfenpyrad, flufenerim and rotenone; (M9) METI II and III compounds selected from the group consisting of acequinocyl, fluacyprim, and hydramethylnon; (M10) uncouplers of oxidative phosphorylation selected from the group consisting of chlorfenapyr and DNOC; (M11) inhibitors of oxidative phosphorylation selected from the group consisting of azocyclotin, cyhexatin, diafenthiuron, fenbutatin oxide, propargite, and tetradifon; (M12) moulting disruptors selected from the group consisting of cyromazine, chromafenozide, halofenozide, methoxyfenozide, and tebufenozide; (M13) synergists selected from the group consisting of piperonyl butoxide and tribufos; (M14) sodium channel blocker compounds selected from the group consisting of indoxacarb, and metaflumizone; (M15) selective feeding blockers selected from the group consisting of crylotie, pymetrozine and flonicamid; (M16) mite growth inhibitors selected from the group consisting of clofentezine, hexythiazox and etoxazole; (M17) chitin synthesis inhibitors selected from the group consisting of buprofezin, bistrifluron, chlorfluazuron, diflubenzuron, flucycloxuron, flufenoxuron, hexaflumuron, lufenuron, novaluron, noviflumuron, teflubenzuron and triflumuron; (M18) lipid biosynthesis inhibitors selected from the group consisting of spirodiclofen, spiromesifen, and spirotetramat; (M19) octapaminergic agonists selected from amitraz; (M20) ryanodine receptor modulators selected from the group consisting of flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M20.1); (M21) isoxazoline compounds selected from the group consisting of 4-[5-(3,5-Dichloro-phenyl)-5-trifluoromethyl-4,5-dihydro-isoxazol-3-yl]-2-methyl-N-pyridin-2-ylmethyl-benzamide (M21.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M21.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M21.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M21.4), 4-[5-(3,5-Dichlorophenyl)-5-trifluoromethyl-4,5-dihydro-isoxazol-3-yl]-N-[(methoxyimino)methyl]-2-methylbenzamide (M21.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M21.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M21.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M21.8); (M22) anthranilamide compounds selected from the group consisting of chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M22.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M22.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M22.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M22.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M22.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M22.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M22.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M22.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M22.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M22.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M22.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M22.12); (M23) malononitrile compounds selected from the group consisting of 2-(2,2,3,3,4,4,5,5-octafluoropentyl)-2-(3,3,3-trifluoropropyl)malononitrile (CF2H—CF2-CF2-CF2-CH2-C(CN)2-CH2-CH2-CF3) (M23.1) and 2-(2,2,3,3,4,4,5,5-octafluoropentyl)-2-(3,3,4,4,4-pentafluorobutyl)-malonodinitrile (CF2H—CF2-CF2-CF2-CH2-C(CN)2-CH2-CH2-CF2-CF3) (M23.2); (M24) microbial disruptors selected from the group consisting of *Bacillus thuringiensis* subsp. *Israelensi*, *Bacillus sphaericus*, *Bacillus thuringiensis* subsp. *Aizawai*, *Bacillus thuringiensis* subsp. *Kurstaki* and *Bacillus thuringiensis* subsp. *Tenebrionis*; (M25) aminofuranone compounds selected from the group consisting of 4-{[(6-Bromopyrid-3-yl)methyl](2-fluoroethyl)amino}furan-2(5H)-on (M25.1), 4-{[(6-Fluoropyrid-3-yl)methyl](2,2-difluoroethyl)amino}furan-2(5H)-on (M25.2), 4-{[(2-Chloro1,3-thiazolo-5-yl)methyl](2-fluoroethyl)amino}furan-2(5H)-on (M25.3), 4-{[(6-Chloropyrid-3-yl)methyl](2-fluoroethyl)amino}furan-2(5H)-on (M25.4), 4-{[(6-Chloropyrid-3-yl)methyl](2,2-difluoroethyl)amino}furan-2(5H)-on (M25.5), 4-{[(6-Chloro-5-fluoropyrid-3-yl)methyl](methyl)amino}furan-2(5H)-on (M25.6), 4-{[(5,6-Dichloropyrid-3-yl)methyl](2-fluoroethyl)amino}furan-2(5H)-on (M25.7), 4-{[(6-Chloro-5-fluoropyrid-3-yl)methyl](cyclopropyl)amino}furan-2(5H)-on (M25.8), 4-{[(6-Chloropyrid-3-yl)methyl](cyclopropyl)amino}furan-2(5H)-on (M25.9) and 4-{[(6-Chloropyrid-3-yl)methyl](methyl)amino}furan-2(5H)-on (M25.10); (M26) botanically-derived oils and compounds selected from the group consisting of cinnamon oil, dill oil, mint oil, thyme oil, anabasine, azadirachtin, d-limonene, cinerin-I, cinerin-II, jasmolin-I, jasmolin-II, pyrethrin-I and pyrethrin-II; (M27) various other compounds selected from the group consisting of amidoflumet, benclothiaz, benzoximate, bifenazate, borax, bromopropylate, cyenopyrafen, cyflumetofen, chinomethionate, dicofol, fluoroacetate, pyridalyl, pyrifluquinazon, tartar emetic, sulfoxaflor, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2), 8-(2-Cyclopropylmethoxy-4-trifluoromethyl-phenoxy)-3-(6-trifluoromethyl-pyridazin-3-yl)-3-aza-bicyclo[3.2.1]octane (M27.3), N—R'-2,2-dihalo-1-R"cyclo-propanecarboxamide-2-(2,6-dichloro-α,α,α-trifluoro-p-tolyl)hydrazone and N—R'-2,2-di(R''')propionamide-2-(2,6-dichloro-α,α,α-trifluoro-p-tolyl)hydrazone, wherein R' is methyl or ethyl, halo is chloro or bromo, R" is hydrogen or methyl and R''' is methyl or ethyl.

6. The ready-to-use foamable pesticide composition as set forth in claim 1 wherein the pesticide is a fungicide selected from the group consisting of respiration inhibitors selected from the group consisting of azoxystrobin, dimoxystrobin, enestroburin, fluoxastro-bin, kresoxim-methyl, meto-minostrobin, orysastrobin, picoxy-strobin, pyraclostrobin, pyrametostrobin, pyraoxystrobin, pyribencarb, trifloxystrobin, methyl(2-chloro-5 [1-(3-methylbenzyl-oxy-imino)-ethyl]benzyl)-carba-mate, 2 (2-(3-(2,6-di-chlorophenyl)-1-methyl-allylidene-aminooxy-methyl)-phenyl)-2-methoxy-imino-N methyl-acetamide, famoxadone, fenamidone, benodanil, bixafen, boscalid, carboxin, fen-furam, fenhexamid, fluopyram, flutolanil, furametpyr, isopyrazam, isotianil, mepronil, oxycarboxin, penflufen, penthiopyrad, sedaxane, tecloftalam, thifluz-amide, tiadinil, 2-amino-4 methyl-thiazole-5-carbox-anilide, N-(3',4',5' tri-fluoro-bi-phenyl-2 yl)-3-difluoro-methyl-1-methyl-1H-pyrazole-4 carboxamide, N-(4'-tri-fluoro-methyl-thiobi-phenyl-2-yl)-3 difluoromethyl-1-methyl-1H pyrazole-4-carbox-amide, N-(2-(1,3,3-trimethyl-butyl)-phenyl)-1,3-dimethyl-5 fluoro-1H-pyrazole-4 carbox-amide, cyazofamid, amisulbrom, diflumetorim, binapacryl, dinobuton, dinocap, fluazinam, nitrthal-isopropyl, tecnazen, ferimzone, fentin salts, ametoctradin and silthiofam; sterol biosynthesis inhibitors (SBI fungicides) selected from the group consisting of azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothio-conazole, simeconazole, tebuconazole, tetraconazole, triadimefon, triadimenol, triticonazole, uniconazole, imazalil, pefurazoate, oxpoconazole, prochloraz, triflumizole, fenarimol, nuarimol, pyrifenox, triforine, aldimorph, dodemorph, dodemorph-acetate, fenpropimorph, tridemorph, fenpropidin, piperalin, spiroxamine, fenhexamid, benalaxyl, benalaxyl-M, kiralaxyl, metalaxyl, metalaxyl-M (mefenoxam), ofurace, oxadixyl, hymexazole, octhilinone, oxolinic acid, bupirimate, benomyl, carbendazim, fuberidazole, thiabendazole, thiophanate-methyl, 5-chloro-7(4-methyl-piperidin-1-yl)-6-(2,4,6-trifluorophenyl)-[1,2,4]tri-azolo-[1,5a]pyrimidine, diethofencarb, ethaboxam, pencycuron, fluopicolide, zoxamide, metrafenone, cyprodinil, mepanipyrim, nitrapyrin, pyrimethanil, blasticidin-S, kasugamycin, kasugamycin hydrochloride-hydrate, mildiomycin, streptomycin, oxytetracyclin, polyoxine, validamycin A, fluoroimid, iprodione, procymidone, vinclozolin, fenpiclonil, fludioxonil, quinoxyfen, edifenphos, iprobenfos, pyrazophos, isoprothiolane, dicloran, quintozene, tecnazene, tolclofos-methyl, biphenyl, chloroneb, etridiazole, dimethomorph, flumorph, mandiproamid, pyrimorph, benthiavalicarb, iprovalicarb, pyribencarb, valifenalate, N-(1-(1-(4-cyano-phenyl)-ethanesulfonyl)-but-2-yl) carbamic acid-(4-fluorophenyl) ester, propamocarb, propamo-carb-hydrochlorid, Bordeaux mixture, copper acetate, copper hydroxide, copper oxychloride, basic copper sulfate, sulfur, ferbam, mancozeb, maneb, metam, methasulphocarb, metiram, propineb, thiram, zineb, ziram, anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide,
guanidine, dodine, dodine free base, guazatine, guazatine-acetate, iminoctadine, iminoctadine-triacetate, iminoctadine-tris(albesilate), dithianon, validamycin, polyoxin B, pyroquilon, tricyclazole, carpropamide, dicyclomet, fenoxanil, acibenzolar-S-methyl, probenazole, isotianil, tiadinil, prohexadione-calcium, fosetyl, fosetyl-aluminum, phosphorous acid and its salts, bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclo-propylmethoxy-imino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-prop-oxy)-phenyl)-N-ethyl-N-methyl formamidine, N'-(5-difluoromethyl-2 methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-meth-yl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester, N-Methyl-2-{1-[(5-methyl-3-trifluoro-methyl-1H-pyr-azol-1-yl)-acetyl]-piperi-din-4-yl}-N-[(1R)-1,2,3,4-tetrahydro-naphthalen-1-yl]-4-thi-azolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-isopropyl-3-oxo-4-ortho-tolyl-2,3-dihydro-pyrazole-1 carbothioic acid S-allyl ester, N-(6-methoxy-pyridin-3-yl) cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimeth-oxy-phenyl)-isox-azol-5-yl]-2-prop-2-ynyloxy-acetamide, abscisic acid, amidochlor, ancymidol, 6-benzylaminopurine, brassinolide, butralin, chlormequat (chlormequat chloride), choline chloride, cyclanilide, daminozide, dike-gulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole, and antifungal biocontrol agents.

7. The ready-to-use foamable pesticide composition as set forth in claim 1 wherein the pesticide is a herbicide selected from the group consisting of acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor, bilanafos, glyphosate, glufosinate, sulfosate, clodinafop, cyhalofop-butyl, fenoxaprop, fluazifop, haloxyfop, metamifop, propaquizafop, quizalofop, quizalofop-P-tefuryl, diquat, paraquat, asulam, butylate, carbetamide, desmedipham, dimepiperate, eptam (EPTC), esprocarb, molinate, orbencarb, phenmedipham, prosulfocarb, pyributicarb, thiobencarb, triallate, butroxydim, clethodim, cycloxydim, profoxydim, sethoxydim, tepraloxydim, tralkoxydim, benfluralin, ethalfluralin, oryzalin, pendimethalin, prodiamine, trifluralin, acifluorfen, aclonifen, bifenox, diclofop, ethoxyfen, fomesafen, lactofen, oxyfluorfen, bomoxynil, dichlobenil, ioxynil, imazamethabenz, imazamox, imazapic, imazapyr, imazaquin, imazethapyr, clomeprop, 2,4-dichlorophenoxy-acetic acid (2,4-D), 2,4-DB, dichlorprop, MCPA, MCPA-thioethyl, MCPB, Mecoprop, chloridazon, flufenpyr-ethyl, fluthiacet, norflurazon, pyridate, aminopyralid, clopyralid, diflufenican, dithiopyr, fluridone, fluroxypyr, picloram, picolinafen, thiazopyr, amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea, ametryn, atrazine, cyanazine, dimethametryn, ethiozin, hexazinone, metamitron, metribuzin, prometryn, simazine, terbuthylazine, terbutryn, triaziflam, chlorotoluron, daimuron, diuron, fluometuron, isoproturon, linuron, metha-benzthiazuron, tebuthiuron, bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam, amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumicloracpentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-

(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester and 4-amino-3-chloro-6-(4-chloro-3-dimethylamino-2-fluoro-phenyl)-pyridine-2-carboxylic acid methyl ester.

8. The ready-to-use foamable pesticide composition as set forth in claim 1 wherein the pesticide is fipronil.

9. The ready-to-use foamable pesticide composition as set forth in claim 8 comprising a fipronil stabilizer compound.

10. The ready-to-use foamable pesticide composition as set forth in claim 1 wherein the composition is characterized by a foam expansion ratio of at least 10:1.

11. The ready-to-use foamable pesticide composition as set forth in claim 1 comprising a preservative.

12. The ready-to-use foamable pesticide composition as set forth in claim 11 wherein the preservative is selected from the group consisting of benzoic acid, sodium benzoate, potassium bicarbonate and mixtures thereof.

13. The ready-to-use foamable pesticide composition as set forth in claim 1 wherein the propellant is dimethyl ether.

14. The ready-to-use foamable pesticide composition as set forth in claim 1 comprising dimethyl ether and carbon dioxide as propellants.

15. The ready-to-use foamable pesticide composition as set forth in claim 1 wherein the composition is characterized by a pH of from about 6.5 to about 8.

16. The ready-to-use foamable pesticide composition as set forth in claim 1 wherein the composition does not contain hydrocarbon propellants other than dimethyl ether.

17. The ready-to-use foamable pesticide composition as set forth in claim 1 wherein the composition does not contain isopropyl alcohol.

18. A pesticide applicator for applying pesticide to a surface, the applicator comprising:
 a container; and
 a ready-to-use foamable pesticide composition as set form in claim 1.

19. A method for controlling pests, the method comprising applying to a surface a ready-to-use pesticide composition as set form in claim 1.

* * * * *